United States Patent
Heath et al.

(10) Patent No.: US 9,230,222 B2
(45) Date of Patent: Jan. 5, 2016

(54) SYSTEM AND METHOD ENABLING BI-TRANSLATION FOR IMPROVED PRESCRIPTION ACCURACY

(75) Inventors: Chester Heath, Boca Raton, FL (US); Pedro Martinez, Boca Raton, FL (US); Noel Guillama, Wellington, FL (US)

(73) Assignees: The Quantum Group, Inc., Lake Worth, FL (US); Noel J. Guillama, Wellington, FL (US)

( * ) Notice: Subject to any disclaimer, the term of this patent is extended or adjusted under 35 U.S.C. 154(b) by 1135 days.

(21) Appl. No.: 12/506,570

(22) Filed: Jul. 21, 2009

(65) Prior Publication Data
US 2010/0023312 A1    Jan. 28, 2010

Related U.S. Application Data

(60) Provisional application No. 61/083,029, filed on Jul. 23, 2008.

(51) Int. Cl.
*G10L 15/00* (2013.01)
*G10L 15/26* (2006.01)
(Continued)

(52) U.S. Cl.
CPC ............ *G06Q 10/00* (2013.01); *G06F 17/2211* (2013.01); *G06F 17/277* (2013.01); *G10L 15/26* (2013.01); *G06F 19/345* (2013.01); *G06F 19/3418* (2013.01); *G06F 19/3437* (2013.01); *G06F 19/3475* (2013.01); *G06F 19/3481* (2013.01)

(58) Field of Classification Search
CPC ..... G10L 15/32; G06F 19/34; G06F 19/3456; G06F 19/3418; G06F 19/3481; G06F 19/3437; G06F 19/345

USPC .......................................... 704/257, 235, 270
See application file for complete search history.

(56) References Cited

U.S. PATENT DOCUMENTS 5,772,585 A * 6/1998 Lavin et al. .................... 600/300
6,167,376 A * 12/2000 Ditzik ............................ 704/235
(Continued)

FOREIGN PATENT DOCUMENTS

WO        WO 92/05517    *    4/1992    ............... G06K 9/22

OTHER PUBLICATIONS

Stelios E. Lambros. Smartpad : A Mobile Multimodal Prescription Filling System. University of Virginia thesis. Mar. 25, 2003.*
(Continued)

*Primary Examiner* — Matthew Baker
(74) *Attorney, Agent, or Firm* — Novak Druce Connolly Bove + Quigg LLP

(57) ABSTRACT

A system for bi-translation of speech and writing is provided. The system can comprise one or more electronic data processors contained within one or more computing devices. The system can also include a module configured to execute on the one or more electronic data processors in order to record a spoken and written segment into the one or more computing devices, where the segments can be corroborated by selecting potential medications and processes. The module can also be configured to convert the spoken segment into a stream of text or tokens and the written segment into a stream of text or tokens. Furthermore, the module can be configured to compare the converted spoken and written streams of text or tokens to determine whether the spoken segment and the written segment match and output the results.

6 Claims, 2 Drawing Sheets

(51) Int. Cl.
  *G10L 21/00* (2013.01)
  *G10L 25/00* (2013.01)
  *G06Q 10/00* (2012.01)
  *G06F 17/22* (2006.01)
  *G06F 17/27* (2006.01)
  *G06F 19/00* (2011.01)

(56) References Cited

U.S. PATENT DOCUMENTS

| | | | | |
|---|---|---|---|---|
| 6,285,785 | B1* | 9/2001 | Bellegarda et al. | 382/187 |
| 6,401,067 | B2* | 6/2002 | Lewis et al. | 704/275 |
| 6,804,654 | B2* | 10/2004 | Kobylevsky et al. | 704/275 |
| 6,889,190 | B2* | 5/2005 | Hegarty | 704/275 |
| 7,058,584 | B2* | 6/2006 | Kosinski et al. | 705/2 |
| 7,133,937 | B2* | 11/2006 | Leavitt | 710/1 |
| 7,137,076 | B2* | 11/2006 | Iwema et al. | 715/863 |
| 7,149,970 | B1* | 12/2006 | Pratley et al. | 715/257 |
| 7,467,089 | B2* | 12/2008 | Roth et al. | 704/270 |
| 7,702,525 | B2* | 4/2010 | Kosinski et al. | 705/2 |
| 7,848,934 | B2* | 12/2010 | Kobylevsky et al. | 705/2 |
| 7,853,446 | B2* | 12/2010 | Allard et al. | 704/9 |
| 7,881,936 | B2* | 2/2011 | Longe et al. | 704/257 |
| 7,957,984 | B1* | 6/2011 | Vallone | 705/2 |
| 8,060,380 | B2* | 11/2011 | Sullivan et al. | 705/2 |
| 8,150,706 | B2* | 4/2012 | Kobylevsky et al. | 705/2 |
| 8,275,613 | B2* | 9/2012 | Harter et al. | 704/235 |
| 8,423,351 | B2* | 4/2013 | Hughes | 704/9 |
| 8,457,959 | B2* | 6/2013 | Kaiser | 704/231 |
| 2002/0035484 | A1* | 3/2002 | McCormick | 705/2 |
| 2002/0099534 | A1* | 7/2002 | Hegarty | 704/2 |
| 2002/0143533 | A1* | 10/2002 | Lucas et al. | 704/235 |
| 2003/0055638 | A1* | 3/2003 | Burns et al. | 704/231 |
| 2003/0182101 | A1* | 9/2003 | Lambert | 704/1 |
| 2003/0233237 | A1* | 12/2003 | Garside et al. | 704/270 |
| 2004/0049388 | A1* | 3/2004 | Roth et al. | 704/251 |
| 2004/0102971 | A1* | 5/2004 | Lipscher et al. | 704/236 |
| 2004/0267528 | A9* | 12/2004 | Roth et al. | 704/251 |
| 2005/0159948 | A1* | 7/2005 | Roth et al. | 704/233 |
| 2005/0234722 | A1* | 10/2005 | Robinson et al. | 704/257 |
| 2005/0283364 | A1* | 12/2005 | Longe et al. | 704/257 |
| 2006/0041427 | A1* | 2/2006 | Yegnanarayanan et al. | 704/235 |
| 2006/0149587 | A1* | 7/2006 | Hill et al. | 705/2 |
| 2006/0167685 | A1* | 7/2006 | Thelen et al. | 704/235 |
| 2007/0067186 | A1* | 3/2007 | Brenner et al. | 705/2 |
| 2008/0077399 | A1* | 3/2008 | Yoshida | 704/208 |
| 2008/0221893 | A1* | 9/2008 | Kaiser | 704/257 |
| 2008/0281582 | A1* | 11/2008 | Hsu et al. | 704/10 |
| 2010/0023312 | A1* | 1/2010 | Heath et al. | 704/2 |
| 2012/0215557 | A1* | 8/2012 | Flanagan et al. | 705/3 |
| 2013/0304453 | A9* | 11/2013 | Fritsch et al. | 704/9 |

OTHER PUBLICATIONS

Scott Durling and Jo Lumsden. 2008. Speech recognition use in healthcare applications. In Proceedings of the 6th International Conference on Advances in Mobile Computing and Multimedia (MoMM '08), Gabriele Kotsis, David Taniar, Eric Pardede, and Ismail Khalil (Eds.). ACM, New York, NY, USA, 473-478.*

Kart, F.; Gengxin Miao; Moser, L.E.; Melliar-Smith, P.M.; , "A Distributed e-Healthcare System Based on the Service Oriented Architecture," Services Computing, 2007. SCC 2007. IEEE International Conference on , vol., no., pp. 652-659, Jul. 9-13, 2007.*

* cited by examiner

100

200

SYSTEM AND METHOD ENABLING BI-TRANSLATION FOR IMPROVED PRESCRIPTION ACCURACY

CROSS-REFERENCE TO RELATED APPLICATIONS

This application claims the benefit of U.S. Provisional Patent Application No. 61/083,029, which was filed Jul. 23, 2008, and which is incorporated herein in its entirety.

FIELD OF THE INVENTION

The present invention is related to the field of computer-based processing, and more particularly, to processing and comparing speech and handwriting.

BACKGROUND OF THE INVENTION

Society has greatly benefited from the many advances in medical knowledge, pharmaceutical drugs, and patient treatments. Despite all these advances, a significant challenge facing the medical field are prescription errors. Prescription errors, due primarily to poor handwriting, are a leading cause of medical errors which lead to injuries and/or fatalities. Currently, when a patient goes to a pharmacy to receive a prescribed drug, the pharmacist often has to read and rely on illegible prescriptions when filling out a particular patient's prescription. This significantly increases the odds that an incorrect drug will be given to the patient. The pharmacist may be able to call the physician directly to verify the prescription, however, often times the physician may be unavailable to communicate with the pharmacist.

In order to more effectively fulfill the healthcare community's obligations to a patient, it is very important to be able to ensure that a patient actually receives what a physician prescribed for the patient's health condition. When patients receive the wrong medications it leads to problems such as health-related complications resulting from taking the wrong medications, decreased trust in the medical system, increased costs, and unnecessary expenditures of healthcare resources. As a result, there is a need for a more effective, efficient, and accurate means of reducing prescription errors through the use of systems and methods for bi-translation of speech and writing so as to verify the accuracy of prescriptions.

SUMMARY OF THE INVENTION

The present invention is directed to systems and methods for processing and translating speech and writing, particular handwriting pertaining to written prescriptions. The comparison of speech and writing enables improved prescription accuracy by alerting a prescriber or other individual of an inaccuracy between the speech and corresponding written text.

One embodiment of the invention is a system for bi-translation of speech and writing. The system can comprise one or more electronic data processors contained within one or more computing devices. The system can also include a module configured to execute on the more or more electronic data processors in order to record a spoken and written segment into the one or more computing devices, where the segments can be corroborated by selecting potential medications and processes. The module can also be configured to convert the spoken segment into a stream of text or tokens and the written segment into a stream of text or tokens. Moreover, the module can be configured to compare the converted spoken and written streams of text or tokens to determine whether the spoken segment and the written segment match and output the results.

Another embodiment of the invention is a computer-based method for bi-translation of speech and writing. The method can include recording a spoken and a written segment into one or more computing devices, where the segments can be corroborated by selecting potential medications and processes. The method can also include converting the spoken segment into a stream of text or tokens and the written segment into a stream of text or tokens. Furthermore, the method can include comparing the converted spoken and written streams of text or tokens to determine whether the spoken segment and the written segment match and outputting the results.

Yet another embodiment of the invention is a computer-readable storage medium that contains computer-readable code, which when loaded on a computer, causes the computer to perform the following steps: recording a spoken and a written segment into one or more computing devices, where the segments can be corroborated by selecting potential medications and processes; converting the spoken segment into a stream of text or tokens and the written segment into a stream of text or tokens; and, comparing the converted spoken and written streams of text or tokens to determine whether the spoken segment and the written segment match and outputting the results.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
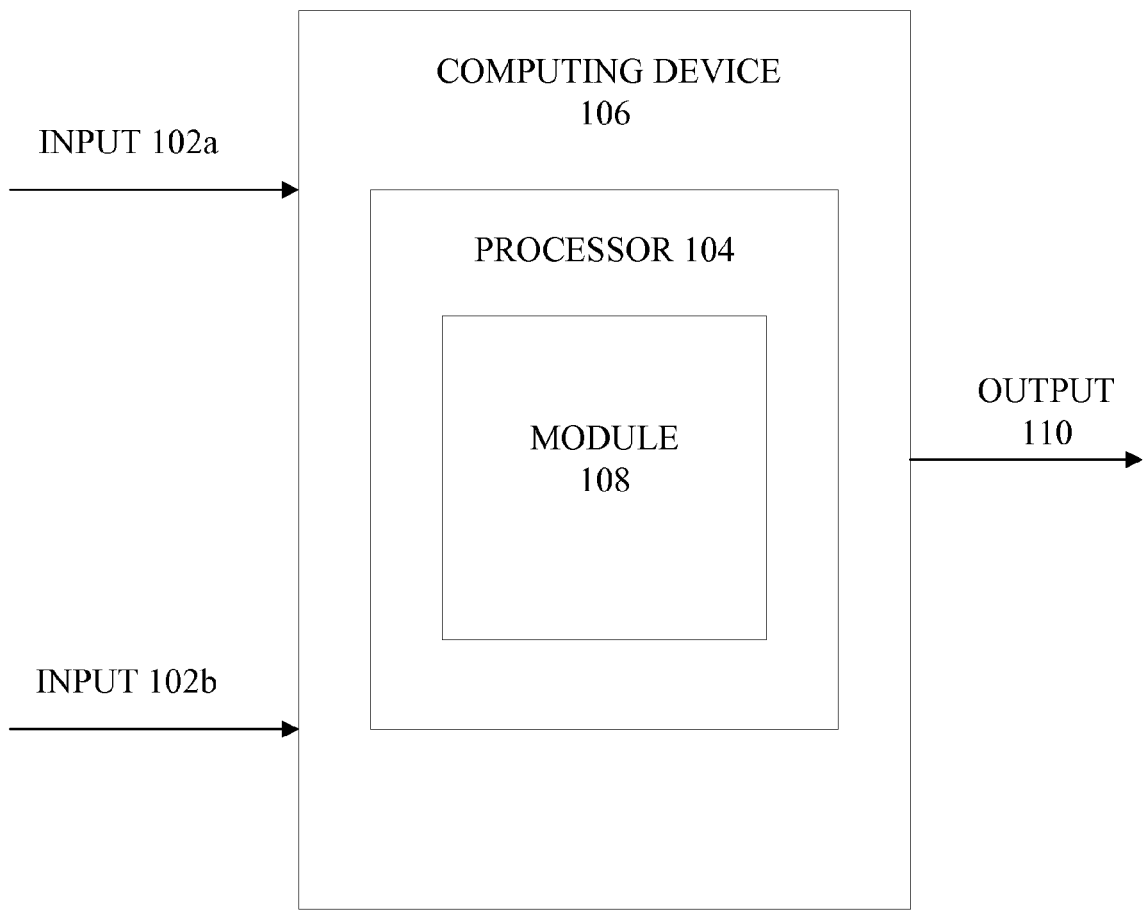
FIG. 1 is a schematic view of a system for bi-translation of speech and writing, according to one embodiment of the invention.

Referring initially to FIG. 1, a system 100 for bi-translation of speech and writing, according to one embodiment of the invention, is schematically illustrated. The system can include one or more speech and writing inputs 102*a-b*. The system 100 further includes one or more electronic data processors 104 contained within one or more computing devices 106. Although two inputs 102*a-b*, one electronic data processor 104, and one computing device 106 are shown, it will be apparent to one of ordinary skill based on the description that a greater or fewer number of inputs 102*a-b* and a greater number of electronic data processors 104 and computing devices 106 can be utilized.

The system 100 further includes a module 108, which, can be implemented as computer-readable code configured to execute on the one or more electronic data processors 104. Alternatively, the module 108 can be implemented in hardwired, dedicated circuitry for performing the operative functions described herein. In yet another embodiment, however, the module 108 can be implemented in a combination of hardwired circuitry and computer-readable code.

Operatively, the module 108 can be configured to record a spoken and written segment, based on the inputs 102*a-b*, into the one or more computing devices 106, where the segments can be corroborated by selecting potential medications and processes. The module 108 can also be configured to convert the spoken segment into a stream of text or tokens and the written segment into a stream of text or tokens. Furthermore, the module 108 can be configured to compare the converted spoken and written streams of text or tokens to determine whether the spoken segment and the written segment match and also generate an output 110 detailing the results.

According to a particular embodiment, the module 108 can be configured to initiate and complete a recording by enabling a user to select one or more icons and characters on the one or more computing devices 106. For example, the computing devices 106 can be an internet tablet, a laptop, a personal digital assistant (PDA), a mobile device, a microphone, a touch screen-enabled device or other computing device. As an illustration, if a user is using a touch-screen enabled device which contains a microphone, the user can select one or more icons and characters on the touch screen that can initiate or complete a recording if the speech and handwriting. The module 108 can also be configured to record the spoken and written segments simultaneously.

According to another embodiment, the module 108 can be further configured to record the spoken and written data segments, that serve as the inputs 102a-b, at separate times, where the beginning and end of each segment are detectable. The module 108 can also be configured to rerecord the spoken and written segments if the beginning and end of each segment are not detectable. For example, if the module cannot determine when the beginning and end of each segment representing a particular prescription are, the module can prompt the user to rerecord the segments.

According to another embodiment, the module 108 can be configured to display the streams of text or tokens as accurate if the streams match and enable a prescriber to verify the results. In yet another embodiment, the module 108 can be further configured to provide an alert and to give a prescriber the option of key entry, selecting the correct text sequence from alternatives shown on the one or more computing devices 106, or selecting from a list of commonly prescribed medications and processes if the streams of text or tokens do not match. As an example, the module 106 can display the converted speech text in black and the converted writing text in red to the user. If the black and red text match, then the user can see that they match and verify the results. However, if the results do not match, then the user is provided with an alert and is given the option of entering in the right prescription, selecting an alternative, or selecting from a list of prescribed medications and processes.

Figure 2:
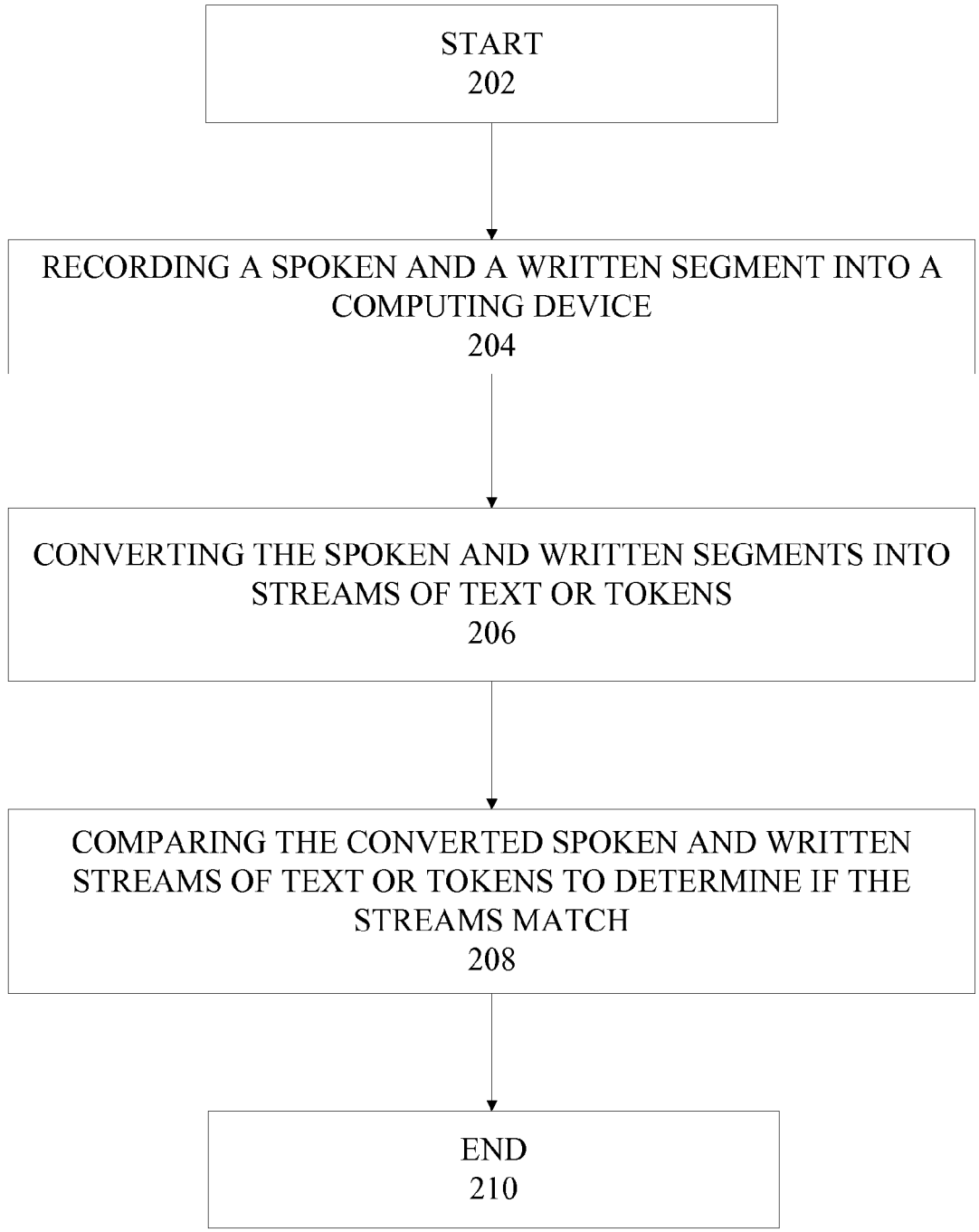
FIG. 2 is a flowchart of steps in a method for bi-translation of speech and writing, according to another embodiment of the invention.

Referring now to FIG. 2, a flowchart is provided that illustrates certain method aspects of the invention. The flowchart depicts steps of a method 200 for bi-translation of speech and writing. The method 200 illustratively includes, after the start step 202, recording a spoken and a written segment into one or more computing devices, where the segments can be corroborated by selecting potential medications and processes at step 204. The method 200 also includes converting the spoken segment into a stream of text or tokens and the written segment into a stream of text or tokens at step 206. At step 208, the method 200 can further include comparing the converted spoken and written streams of text or tokens to determine whether the spoken segment and the written segment match and outputting the results. The method 200 illustratively concludes at step 210.

According to another embodiment, the method 200 can further include, at the recording step 204, initiating and completing a recording by selecting one or more icons and characters on the one or more computing devices. Additionally, the recording step 204 can comprise speaking and writing the segments simultaneously into the one or more computing devices. The recording step 204 can further comprise speaking and writing segments at separate times into the one or more computing devices, where the beginning and end of each segment are detectable.

In one embodiment, the method 200 can include rerecording the spoken and written segments into the one or more computing devices if the beginning and end of each segment are not detectable. According to another embodiment, the method 200 can further include displaying the streams as accurate and enabling a prescriber to verify the results if the streams of text or tokens match. The method 200 can further include providing an alert and enabling a prescriber the option of keying in an entry, selecting the correct text sequence from alternatives shown on the one or more computing devices, or selecting from a list of commonly prescribed medications and processes if the streams of text or tokens do not match.

The invention, as already mentioned, can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, defining a computer program, which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding description of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A computer-based method for bi-translation of speech and writing, the method comprising:
 recording, at separate times, a spoken segment and a written segment from a prescriber into at least one computing device, wherein the spoken segment and the written segment can be corroborated by selecting potential medications and processes, the written segment comprising handwriting, the recording comprising determining that a beginning and an end of each of the spoken segment and the written segment are undetectable and, in response to determining that the beginning and the end of each of the spoken segment and the written segment are undetectable, prompting the prescriber to re-record the spoken segment and the written segment;

converting the spoken segment into a first stream of text or tokens and the written segment into a second stream of text or tokens;

comparing the first stream and the second stream to determine whether the spoken segment and the written segment match and concurrently displaying the first stream and the second stream;

in response to determining that the spoken segment and the written segment match, configuring the at least one computing device to permit a prescriber to verify, via the at least one computing device, the results of the comparing; and in response to determining that the spoken segment and the written segment do not match, providing an alert for the prescriber at the at least one computing device and configuring the at least one computing device to permit a prescriber to select, via the at least one computing device, the correct text sequence from alternatives displayed on the at least one computing device and a correct medication for the text sequence from a list of medications displayed on the at least one computing device.

2. The method of claim 1, wherein the recording step is initiated and completed by selecting at least one of icons and characters on the at least one computing device.

3. A computer-based system for bi-translation of speech and writing, the system comprising:

at least one electronic data processor contained within at least one computing device; and a module configured to execute on the at least one electronic data processor, wherein the module is configured to:

record, at separate times, a spoken segment and written segment from a prescriber into the at least one computing device, wherein the spoken segment and the written segment can be corroborated by selecting potential medications and processes, the written segment comprising handwriting, the recording comprising determining that a beginning and an end of each of the spoken segment and the written segment are undetectable and, in response to determining that the beginning and the end of each of the spoken segment and the written segment are undetectable, prompting the prescriber to re-record the spoken segment and the written segment;

convert the spoken segment into a first stream of text or tokens and the written segment into a second stream of text or tokens;

compare the first stream to the second stream to determine whether the spoken segment and the written segment match and concurrently display the first stream and the second stream;

in response to determining that the spoken segment and the written segment match, configure the at least one computing device to permit a prescriber to verify, via the at least one computing device, the results of the comparing; and in response to determining that the spoken segment and the written segment do not match, provide an alert for the prescriber at the at least one computing device and configure the at least one computing device to permit a prescriber to select, via the at least one computing device, the correct text sequence from alternatives displayed on the at least one computing device and a correct medication for the text sequence from a list of medications displayed on the at least one computing device.

4. The system of claim 3, wherein the module is configured to initiate and complete a recording by enabling a user to select at least one of icons and characters on the at least one computing device.

5. A non-transitory computer-readable storage medium having stored therein computer-readable instructions, which, when loaded in and executed by a computer causes the computer to perform the steps of:

recording, at separate times, a spoken segment and a written segment from a prescriber into at least one computing device, wherein the spoken segment and the written segment can be corroborated by selecting potential medications and processes, the written segment comprising handwriting, the recording comprising determining that a beginning and an end of each of the spoken segment and the written segment are undetectable and, in response to determining that the beginning and the end of each of the spoken segment and the written segment are undetectable, prompting the prescriber to re-record the spoken segment and the written segment;

converting the spoken segment into a first stream of text or tokens and the written segment into a second stream of text or tokens;

comparing the first stream and the second stream to determine whether the spoken segment and the written segment match and concurrently displaying the first stream and the second stream;

in response to determining that the spoken segment and the written segment match, configuring the at least one computing device to permit a prescriber to verify, via the at least one computing device, the results of the comparing; and in response to determining that the spoken segment and the written segment do not match, providing an alert for the prescriber at the at least one computing device and configuring the at least one computing device to permit a prescriber to select, via the at least one computing device, the correct text sequence from alternatives displayed on the at least one computing device and a correct medication for the text sequence from a list of medications displayed on the at least one computing device.

6. The non-transitory computer-readable storage medium of claim 5, wherein the recording step is initiated and completed by selecting at least one of icons and characters on the at least one computing device.

* * * * *